United States Patent [19]

Watari et al.

[11] Patent Number: 5,323,806
[45] Date of Patent: Jun. 28, 1994

[54] CONSTANT-SPEED EXHAUST VALVE DEVICE FOR HEMADYNAMOMETER

[75] Inventors: Yoshie Watari; Mitsuo Nakatani; Satoshi Nakayama; Makoto Fujiwara; Shigeki Sasaki, all of Kadoma, Japan

[73] Assignee: Matsushita Electric Works, Ltd., Osaka, Japan

[21] Appl. No.: 33,740

[22] Filed: Mar. 22, 1993

[30] Foreign Application Priority Data

| Mar. 26, 1992 | [JP] | Japan | 4-068865 |
| Apr. 23, 1992 | [JP] | Japan | 4-103375 |
| Oct. 2, 1992 | [JP] | Japan | 4-265158 |

[51] Int. Cl.⁵ ............................ A61B 5/02
[52] U.S. Cl. ............................ 137/504; 128/685; 137/517; 137/848; 138/45
[58] Field of Search ............. 128/685; 137/504, 517, 137/848; 138/45

[56] References Cited

U.S. PATENT DOCUMENTS

| 2,948,300 | 8/1960 | Fraser | 137/517 X |
| 5,027,823 | 7/1991 | Sanaka | 128/685 |
| 5,031,631 | 7/1991 | Kawamura | 128/685 |

FOREIGN PATENT DOCUMENTS

| 3117546 | 10/1982 | Fed. Rep. of Germany | 128/685 |
| 3526536 | 1/1987 | Fed. Rep. of Germany | 128/685 |

Primary Examiner—Robert G. Nilson
Attorney, Agent, or Firm—Kenyon & Kenyon

[57] ABSTRACT

A constant-speed exhaust valve device has a valve body of a cylindrical shape opened at both axial ends, and a push means disposed to apply an axial compressive force to the valve body, whereby the exhaust speed of the device can be made steady and manufacturing yield of the device is made excellent.

9 Claims, 7 Drawing Sheets

FIG. 3
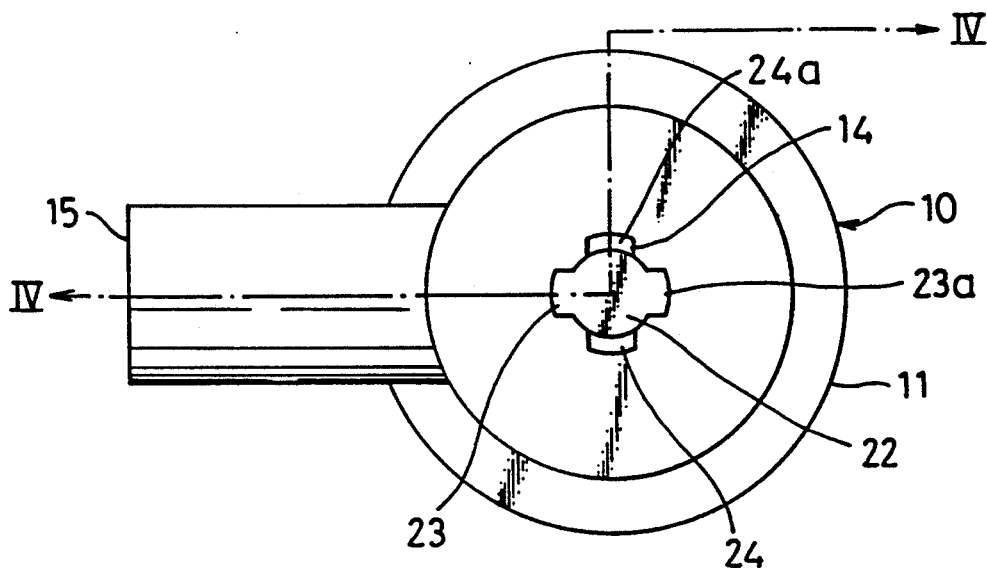
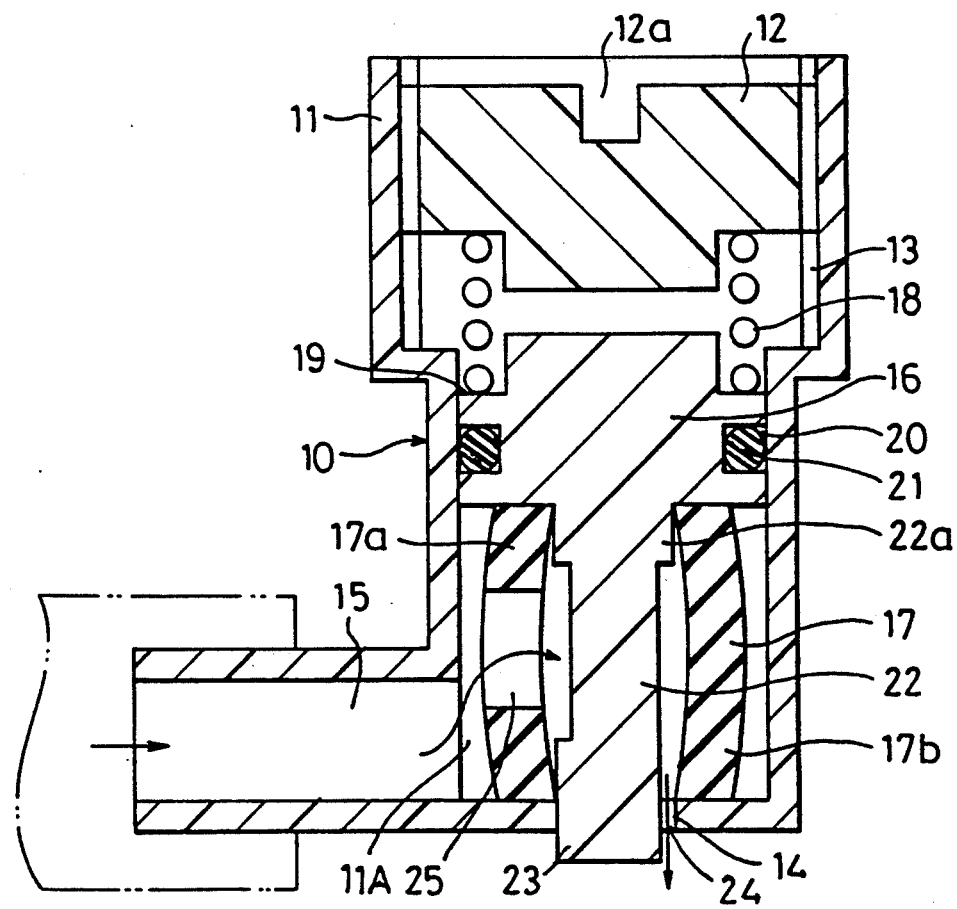
FIG. 4

FIG. 7
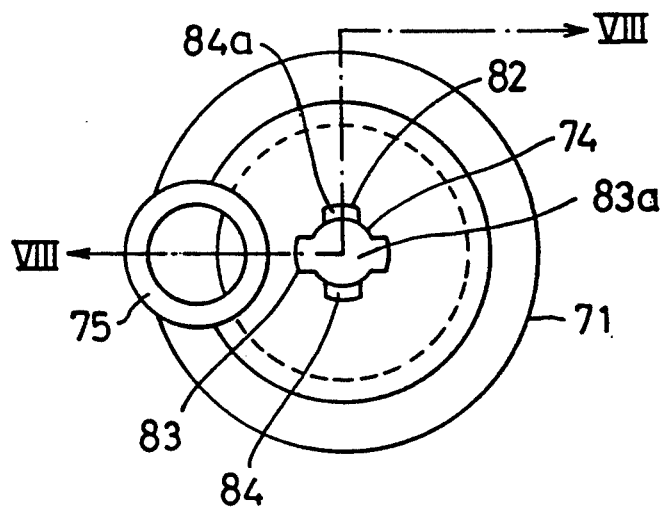
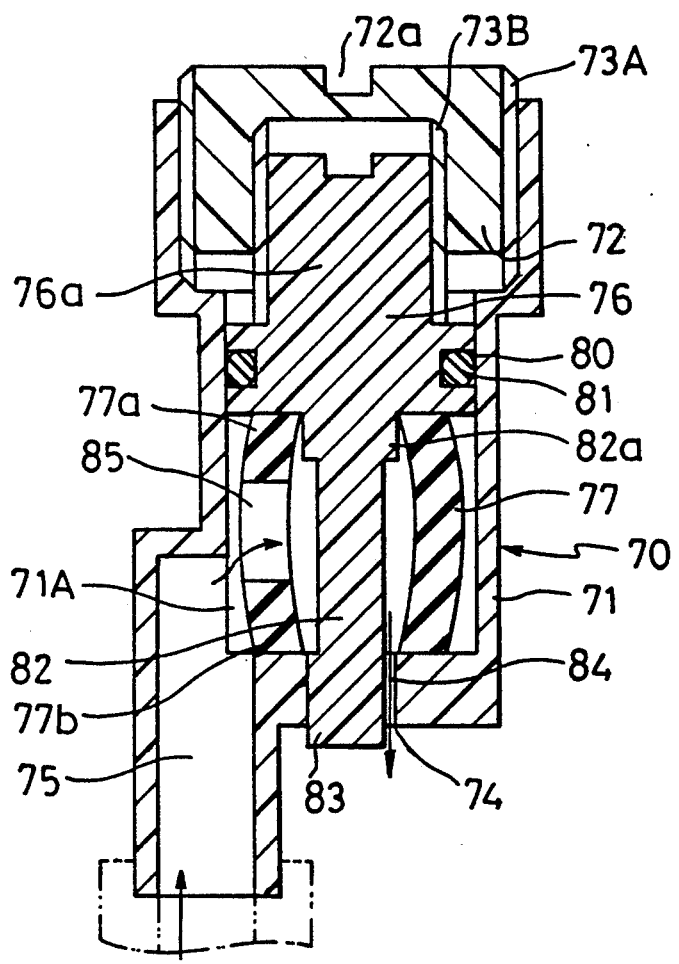
FIG. 8

FIG. 9
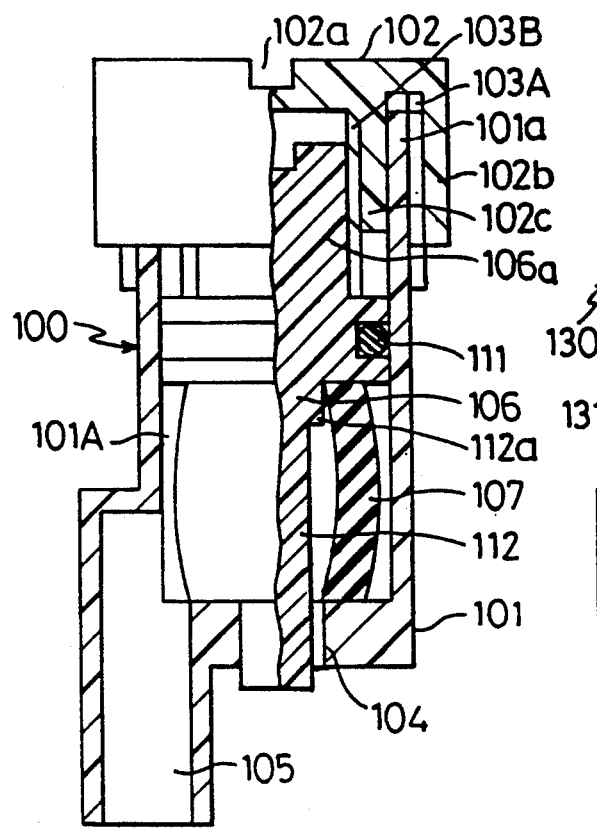
FIG. 10
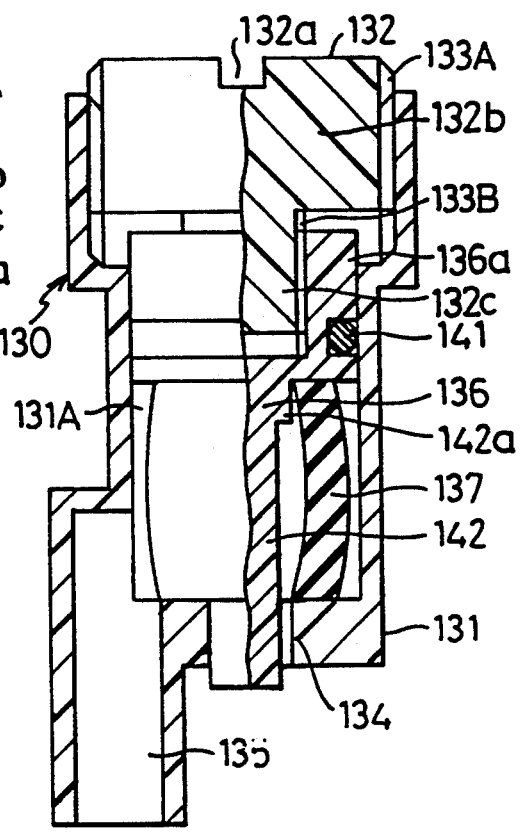
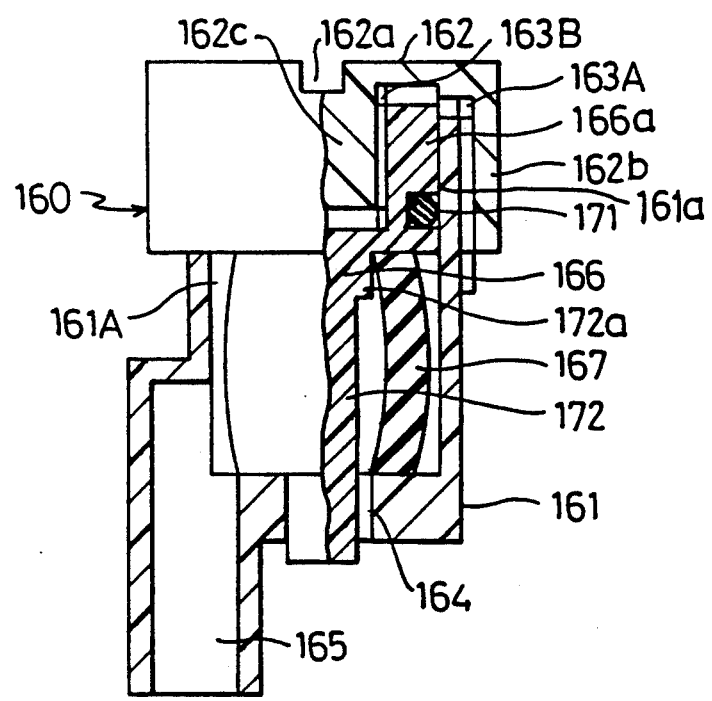
FIG. 11

CONSTANT-SPEED EXHAUST VALVE DEVICE FOR HEMADYNAMOMETER

BACKGROUND OF THE INVENTION

This invention relates to a constant-speed exhaust valve device for hemadynamometers and, more particularly, to the constant-speed exhaust valve device capable of reducing pneumatic pressure at a constant speed for hemadynamometry to be contributive to effective measurement of human blood pressure.

DESCRIPTION OF RELATED ART

In the hemadynamometer for measuring the blood pressure in a socalled oscillometric process, a cuff wound on an upper arm or the like is pressurized to a predetermined pressure level by means of an air pump to have an artery oppressed to occlude blood flow, thereafter the pressure in the cuff is gradually lowered by means of a constant-speed exhaust valve device, during which patterns of the cuff pressure and oscillation amplitude accompanying arterial pulsation are processed by means of a microcomputer, and thereby the highest and lowest blood pressure values are determined. For the constant-speed exhaust valve device employed in the hemadynamometer of the kind referred to, it has been desired that the device is capable of dropping the cuff pressure linearly with time at a constant-speed of about 3 to 4 mmHg/sec.

For conventional constant-speed exhaust valve device, examples of the device have been disclosed in Japanese Utility Model Publication No. 63-14809, Japanese Patent Laid-Open Publication No. 57-14321 and so on, which respectively comprise a valve body formed by an elastic material into a bottomed cylindrical shape, i.e., a cup shape, which valve body being provided with a slit extending in longitudinal direction in a side wall, and a push member engaged to open end side having a flange of the valve body for adjusting opening rate of the slit, so as to allow the exhaust to take place through the slit and push member.

On the other hand, required characteristics of exhaust air rate Q (cc/min) with respect to the pressure P (mmHg) of the constant-speed exhaust valve device for attaining a desired pressure drop rate in the cuff, that is, the P-Q characteristics are theoretically required to draw an exponential curve such as shown by a curve A in FIG. 1 in which the degree of increment in the exhaust air rate Q becomes large as the pressure P decreases. In the above described conventional device, here, the pressure P which is high will cause the valve body made of the elastic material to be subjected at its outer periphery to a high compressive force to minimize the opening rate of the slit, and the exhaust rate through such slit becomes smaller. When the pressure P decreases, the compressive force applied to the outer periphery of the valve body is reduced, the valve body is enlarged in the opening rate of the slit by its own stability of the elasticity, and the slit becomes larger to increase the exhaust rate. Accordingly, the foregoing conventional device shows the P-Q characteristics partly closely resembling the curve A of FIG. 1, whereas in an event when the pressure P decreases to be below a certain value the opening rate of the slit does not vary any more. Therefore, as shown by another curve B in FIG. 1, the characteristics are caused to be largely deviated from the theoretical value, in the event where the pressure P is low. In respect of the hemadynamometry, however, the influence is not remarkable, and the foregoing conventional device has been regarded optimum in view of its simplicity in the structure.

However, the foregoing known devices still involve such drawbacks as in the followings. That is, while it is general that the valve body of the bottomed cylindrical shape or of the cup shape to be closed at one axial end is molded with upper and lower dies, the thickness of the side wall in which the slit is to be formed is determined by relative position between the upper and lower dies, so that there will arise a risk that the side wall is not uniform in the thickness but is uneven. Since a large number of the valve bodies are formed in a mass production scale generally with the dies of single type, the tendency of causing such risk of uneven thickness is further increased.

With the valve body having the slit in such side wall of uneven thickness, the presence of the uneven thickness adjacent the slit should result in inequality of the opening rate of the slit even upon equal application of the pressure P, and the P-Q characteristics of the valve body would be remarkably different from those in the case where no uneven thickness is present such as shown by a curve C in FIG. 2. In the case where the slit is formed in a side wall part made thin in the valve body, the opening rate of the slit with respect to a predetermined pressure is made larger, the exhaust rate becomes excessive as represented by a curve D in FIG. 2 in contrast to the curve C of no uneven thickness, whereas the slit formed in a side wall part made thick will result in that the opening rate of the slit with respect to the predetermined pressure is made smaller and the exhaust rate is made excessively smaller as shown by a curve E in FIG. 2 in contrast to the curve C of no uneven thickness. Provided, therefore, that the constant-speed exhaust valve device is prepared with the valve body involving the uneven thickness, the cuff pressure dropping rate should result in a remarkable difference from a target value, any incremental and decremental adjustment of the opening .rate of the slit with the application of the axial force to the valve member by the push member would not be able to set the predetermined voltage drop rate, and still the problem that the manufacturing yield is poor would be left unsolved.

When an adjusting screw is employed as the push member for pushing the valve body, further, a tip end of the adjusting screw is brought into engagement with the open end of the valve body upon pushing the same so that any change in fastening amount of the adjusting screw as the push member will be made directly as the pushing force applied to the valve body, and there will arise a problem that even a slight rotation of the screw results in a remarkable change in the opening rate of the slit so as to render a fine adjustment to be different. It may be possible on the other hand to adopt an arrangement in which the slit is opened when the valve body is deformed to a large extent, but this will result in another problem that the adjusting screw as the push member is required to be rotated many times so that adjusting action will be time-consuming, While a fine adjustment is made easier. In employing the adjusting screw as the push member, further, the fastening motion of the screw causes a twisting force in rotating direction of the screw is applied to the valve body, and this will cause a further drawback to arise in that a deformation may occur at opening edge of the slit and the adjusting action is disordered.

SUMMARY OF THE INVENTION

A primary object of the present invention is, therefore, to provide a constant-speed exhaust valve device which has removed the foregoing problems in the known devices and is capable of rendering the exhaust rate to be constant, attaining an excellent manufacturing yield, and realizing the adjustment towards a predetermined exhaust speed easily, quickly and very finely.

According to the present invention, the above object can be realized by a constant-speed exhaust valve device comprising a valve body made of an elastic material and having a slit of a variable opening rate in accordance with a fluid pressure applied externally, and a push means disposed for pushing the valve body to adjust the opening rate of the slit, the valve body and push means being disposed axially movably in a casing which has an inlet port to be coupled to a cuff of an associated hemadynamometer, wherein the valve body is formed in a cylindrical shaped opened at both axial ends, and the push means is provided for applying a compressive force to the valve body in its axial direction.

Other objects and advantages of the present invention shall be made clear as the following description of preferred embodiments shown in accompanying drawings advances.

BRIEF DESCRIPTION OF THE DRAWINGS

FIG. 3 shows in a bottom plan view the constant-speed exhaust valve device according to the present invention;

FIG. 4 is a sectioned view taken along line IV—IV in FIG. 3 of the device shown in FIG. 3;

FIG. 7 shows in a bottom plan view still another embodiment of the device according to the present invention;

FIG. 8 is a sectioned view taken along line VIII—VIII in FIG. 7 of the device shown in FIG. 7;

FIGS. 9 to 11 show in partly sectioned elevations further embodiments of the device according to the present invention;

Figure 1:
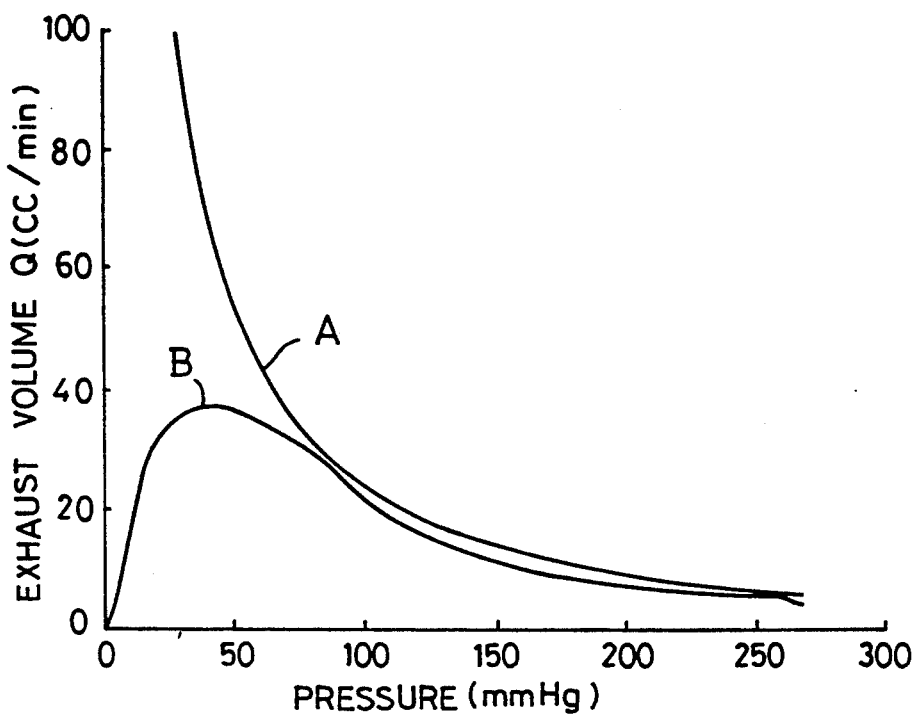
FIGS. 1 and 2 are graphs showing respective relationship between applied pressure and exhaust amount in general exhaust valve devices.
Figure 2:
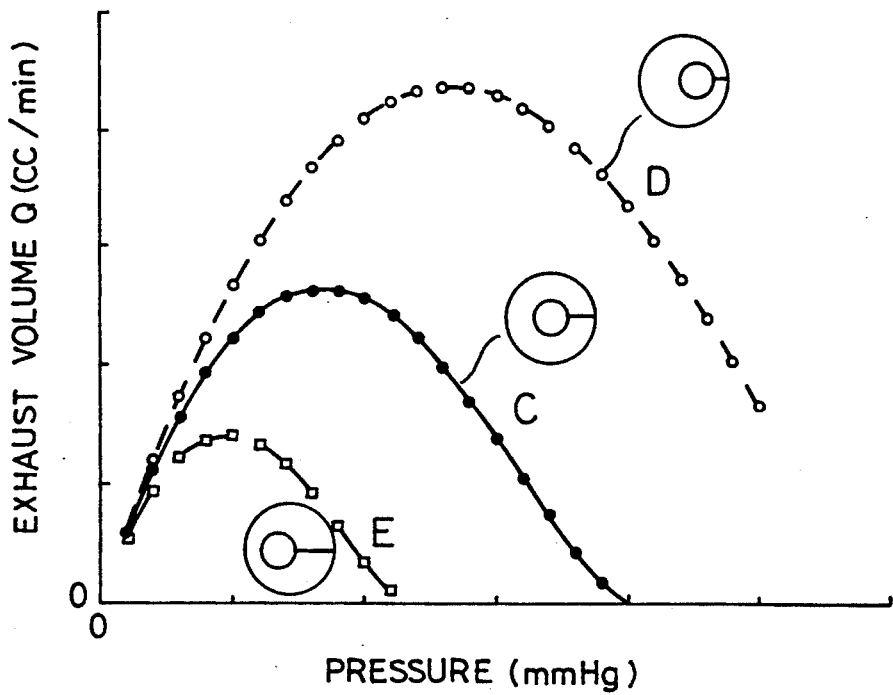

While the present invention shall now be described with reference to the preferred embodiments shown in the drawings, it will be appreciated that the intention is not to limit the invention only to these embodiments shown but rather to include all possible alterations, modifications and equivalent arrangement within the scope of appended claims.

DETAILED DESCRIPTION OF THE PREFERRED EMBODIMENTS

Figure 4A:
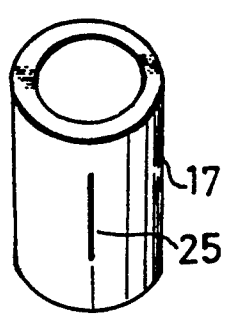
FIG. 4a is a fragmentary perspective view of the valve body in the device of FIG. 3.

Referring to FIGS. 3 and 4, there is shown an embodiment of the constant-speed exhaust valve device according to the present invention, in which this valve device 10 comprises a casing 11 generally of a bottomed cylindrical shape, which casing 11 has a threaded part 13 at upper inner periphery of an open end side for screwing therein an adjusting screw 12, a substantially cruciform through hole 14 in the other bottomed end closed, and an inlet port 15 formed as projected from a lower side face 11A for coupling to a cuff of an associated hemadynamometer (not shown). The adjusting screw 12 has in its upper surface a recess 12a formed to allow a jig for rotating the adjusting screw 12 to be inserted therein.

In the casing 11, there are housed a push means 16 and a valve body 17, while a coil spring 18 is disposed between the adjusting screw 12 and the push means 16 to apply a spring load onto an upper shoulder 19 of the push means 16. An annular peripheral recess 20 is formed in the push means 16 adjacent to the shoulder 19, and an O-ring 21 is accommodated in the recess 20 for air-tightly sealing between inner periphery of the casing 11 and outer periphery of the push means 16. To a lower part of the push means 16, a shaft part 22 is provided for penetrating through the valve body 17 to hold it on the push means 16, and a pair of diametrally opposing projections 23 and 23a are provided at lower end of the shaft part 22 so as to engage in one pair of opposing grooves of the cruciform through hole 14 for stopping axial rotation of the push means 16. In this case, the other pair of opposed grooves of the through hole 14 left not engaged by the projections 23 and 23a of the push means 16 are made to function as exhaust ports 24 and 24a.

The valve body 17 is formed by such elastic material as rubber into a cylindrical shape opened at both axial ends, and is provided with a normally closed slit 25 made through peripheral wall to extend in the axial direction. This slit 25 may be provided in a plurality, in which event the number and the length of the slits 25 are so set as to obtain a predetermined exhaust rate in relation to a volume of the cuff coupled to the inlet port 15, taking into account that the exhaust rate or volume is made larger when the slits 25 are made larger in the length and the number. Thus the valve body 17 can be held between the inner bottom face of the closed end of the casing 11 and the push means 16 under a proper compressive force which can be adjusted by rotating the adjusting screw 12 in the upper part of the casing 11 to thereby vary optimumly the spring load of the coil spring 18. In this case, the valve body 17 has at its upper end 17a an inner diameter substantially equal to an outer diameter at a preferably slightly enlarged upper end part 22a of the shaft part 22, so that the valve body 17 can be reliably held on the shaft part 22. A lower end 17b of the valve body 17 is at least partly separated slightly from outer periphery of lower end part of the shaft part 22, so as to define an exhaust path from the inlet port 15 through the slit 25 to the exhaust ports 24 and 24a.

While in the above the valve body 17 has been referred to as being formed in the cylindrical shape, it may be of any shape so long as the same is opened at both axial ends and is capable of defining its inner and outer surfaces with a single die (without requiring the upper and lower dies) upon manufacturing the valve body 17, including a hollow n-prism or circular cone having a tapered outer periphery. In this case, as will be readily appreciated, the valve body 17 in any of such various shapes will have just a small variation in the thickness in axial directions, in order that a linear relationship is maintained between the pressure applied to the valve body 17 and the opening rate of the slit 25.

In the constant-speed exhaust valve device 10 of the embodiment as has been described above, the adjusting screw 12 is moved downward to properly elevate the spring load of the coil spring 8, the push means 16 is resiliently moved downward to cause the valve body 17 to deform into a barrel shape with axially central part bulged outward as shown in FIG. 4, and the slit 25 is caused thereby to be opened. At this time, the opening rate of the slit 25 corresponds to the compressive force applied to the valve body 17, and the adjusting action of the adjusting screw 12 allows the opening rate of the slit 25 to be adjusted to attain a predetermined exhaust speed. Since in this case the valve body 17 is compressed not directly by the adjusting screw 12 but through the coil spring 18 interposed, in adjusting the opening rate of the slit 25, it is made possible to set a pushing amount of the valve body 17 per each rotation of the adjusting screw 12 to a value not definable by a tooth pitch of the adjusting screw 12 but by means of a selection of spring constant of the coil spring 18. Further, since the push means 16 disposed between the coil spring 18 and the valve body 17 is restricted from being axially rotated by the engagement of the lower end of the shaft part 22 in the through hole 14 of the casing 11 but is allowed to move only in axial direction, the valve body 17 is effectively prevented from being subjected to a twisting force accompanying the rotation of the adjusting screw 12.

In the constant-speed exhaust valve device 10 according to the foregoing embodiment, a highly pressurized air in the cuff is applied through the inlet port 15 to the outer periphery of the valve body 17. Since the interior of the valve body 17 is communicating with the atmosphere through the exhaust ports 24 and 24a so as to be at the atmospheric level, the valve body 17 is caused to be resiliently deformed inward by the pressure difference between both pressures so as to close the slit 25, and an exhaust air amount from the slit 25 through the exhaust ports 24 and 24a to the exterior is reduced. As the pressurized air from the cuff decreases, the valve body 17 is caused to bulge outward by the spring load of the spring 18 acting through the push means 16 so as to open the slit 25 increasingly, and a ventilating rate therethrough is increased. In this case, outer peripheral space around the valve body 17 and upper space above the push means 16 are tightly isolated by means of the O-ring 21, while the lower end of the valve body 17 tightly engages the inner bottom face of the casing 11, and the air tightness of the outer peripheral space of the valve body 17 is maintained.

Figure 5:
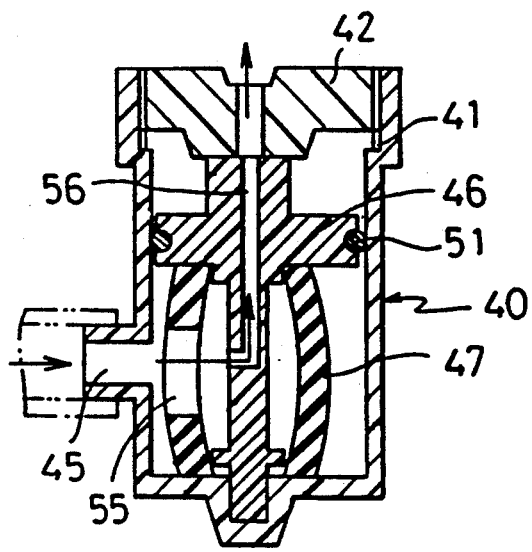
FIG. 5 shows in a similar sectioned view another embodiment of the device according to the present invention.

In the constant-speed exhaust valve device 40 in another embodiment shown in FIG. 5 according to the present invention, the push means 46 is supported within the casing 41 in the rotation-stopped manner at the lower end with respect to the inner bottom face of the casing but in axially shiftable manner. The adjusting screw 42 is brought into engagement directly with the push means 46, without interposition of any spring, so that the push means 46 will axially shift accompanying the axial movement of the adjusting screw 42 to adjust the opening rate of the slit 55 in the valve body 47. An axial exhaust path 56 is formed through the push means 46 and through the adjusting screw 42 so that, when the slit 55 is opened, the pneumatic pressure from the inlet port 45 coupled to the cuff will pass through this path 56 to the exterior. The upper interior space above the push means 56 and the peripheral space around the valve body 47 within the casing 41 are mutually airtightly isolated by the O-ring 51. Other constituents and functions of the present embodiment are substantially the same as those in the foregoing embodiment of FIGS. 3 and 4.

Figure 6:
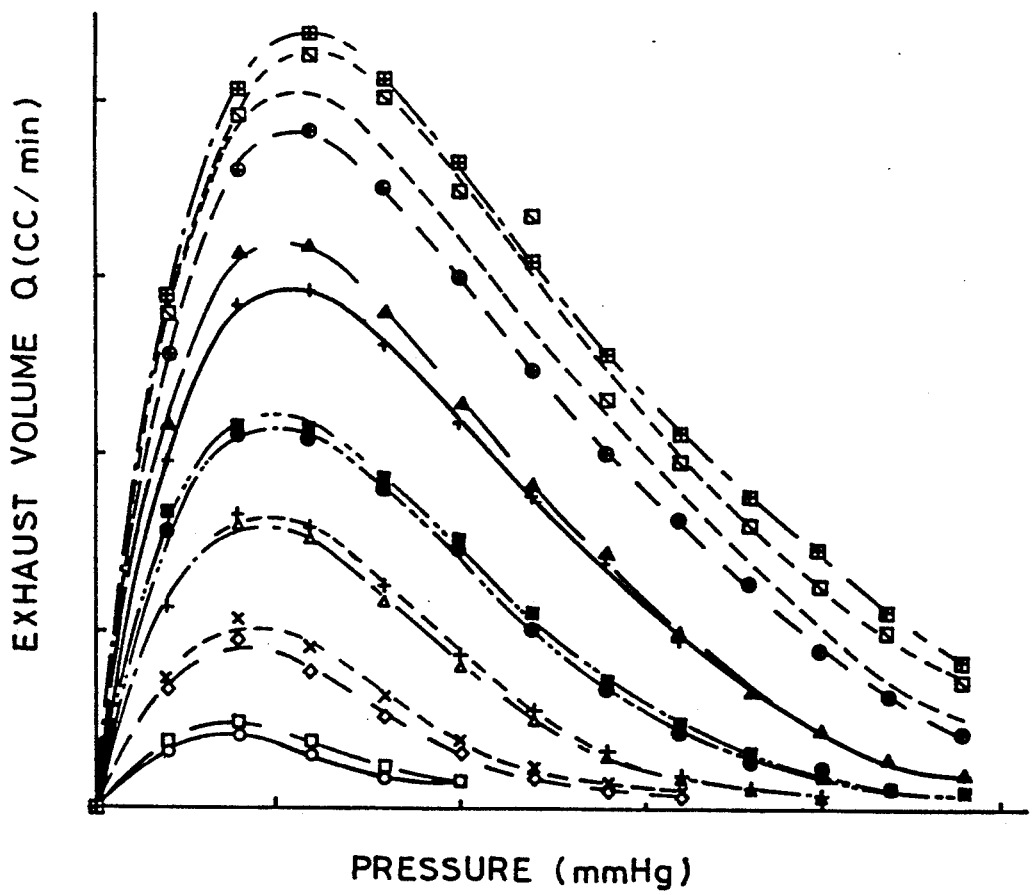
FIG. 6 is a graph showing the relationship between the applied pressure and the exhaust amount in the respective devices shown in FIGS. 3 to 5.

It should be appreciated that, in the constant-speed exhaust valve devices 10 and 40 shown in FIGS. 3 and 4 and in FIG. 5, the P-Q characteristics can be relatively linearly adjusted as shown in FIG. 6.

Referring next to FIGS. 7 and 8, there is shown the constant-speed exhaust valve device 70 in still another embodiment according to the present invention, in which the adjusting screw 72 screwed through a first threaded part 73A into the upper part of the bottomed cylindrical casing 71 is screw-coupled to the push means 76 through a second threaded part 73B which comprises screw-threads formed on inner periphery of an inner axial recess made in the adjusting screw 72 and engaging screw-threads formed on outer periphery at upper part 76a of the push means 76. The first and second threaded parts 73A and 73B are made identical in the rotating direction, but to have different tooth pitch.

Now, in this constant-speed exhaust valve device 70, the adjusting screw 72 is rotated to shift the push means 76 down, then the valve body 77 is deformed into the barrel shape as seen in FIG. 8, the slit 85 in the valve body 77 is opened thereby and the highly pressurized air from the cuff through the inlet port 75 to the opened slit 75 is discharged from the exhaust ports 84 and 84a. The compressive force applied to the valve body 77 is varied in accordance with the lowering amount of the adjusting screw 72, the opening rate of the slit 85 is varied thereby and the exhaust rate is adjusted.

Here, if the first threaded part 73A is made of right hand screw and at a pitch P1 and the second threaded part 73B is made also of the right hand screw but at a different pitch P2, a rightward rotation of the adjusting screw 72 causes this screw to go down towards the valve body 77 at the pitch P1. At this time, a pair of the projections 83 and 83a at the lower end of the push means 76 are engaged in one pair grooves of the cruciform through hole 74 so as to prevent the push means 76 from being axially rotated, and the push means 76 is moved upward as the adjusting screw 72 is rotated. With the rotation of the adjusting screw 72, therefore, the push means 76 is made to shift at a pitch of P1-P2 so that, when it is made that P1>P2 and the difference between P1 and P2 is made smaller, the axial shift amount of the push means 76 responsive to rotating angle of the adjusting screw 72 can be made small, whereby the opening rate of the slit 85 can be varied bit by bit with a relatively wide rotating angle of the adjusting screw 72, and a required adjustment for a predetermined exhaust speed can be made easier.

Provided that the pitch P1 of the first threaded part 73A and the pitch P2 of the second threaded part 73B are so set as to be P1<P2, it is made possible to move the push means 76 downward by means of a rotation of the adjusting screw 72 in a direction for moving it upward, so as to compress the valve body 77. In assembling the constant-speed exhaust valve device 70 of this arrangement, the adjusting screw 72 and push means 76 in the state of screw-coupled together at the second threaded part 73B are put into the casing 71 having already therein the valve body 77, to insert from above the shaft part 82 of the push means 76 through the cylindrical valve body 77 while screwing the adjusting screw 72 into the casing 71 at the first threaded part 73A, the projections 83 and 83a at the lower end of the shaft part 82 of the push means 76 are engaged in the through hole 74 in the bottom of the casing to stop the rotation of the push means 76, upon which the adjusting screw 72 is rotated in reverse direction in which the first threaded part 73A is unfastened, then the push means 76 is moved downward to compress the valve body 77, and the assembling is thereby completed with the assembling work thus made extremely easier.

While in the constant-speed exhaust valve device 70 of the foregoing embodiment the first and second threaded parts 73A and 73B have been referred to as having the screw threads made mutually in the same direction, it would be possible to provide these threaded parts to be of opposite rotary directions. That is, when the first threaded part 73A has a right hand screw of a pitch P1, the second threaded part 73B is made to have a left hand screw of a pitch P2. In this event, a rightward rotation, for example, of the adjusting screw 72 causes the screw itself to move downward at the pitch P1 with respect to the first threaded part 73A and also at the pitch P2 with respect to the second threaded part 73B, and eventually the push means 76 is lowered at a composite pitch P1+P2. Accordingly, it is made possible to increase the shift amount of the push means 76 responsive to the rotary angle of the adjusting screw 72, that is, a remarkable adjusting in the shift amount of the push means 76 can be realized by a slight rotation of the adjusting screw 72.

While in the embodiment of FIGS. 7 and 8 the inlet port 75 is shown to lie in parallel direction to the axial direction of the push means 76, the same may be provided in the same manner as in the case of FIGS. 3 and 4 or FIG. 5 as required. Other constituents and function than those referred to are the same as those in the embodiment of FIGS. 3 and 4, and substantially the same constituents as the ones shown in FIGS. 3 and 4 are shown in FIGS. 7 and 8 with the same reference numerals but as added by 60.

In another embodiment shown in FIG. 9 according to the present invention, the adjusting screw 102 of the constant-speed exhaust valve device 100 is provided to have double, coaxial cylindrical walls 102b and 102c, and an upper end part 101a of the casing 101 is inserted between these cylindrical walls 102b and 102c and screw-coupled to outer-positioned cylindrical wall 102b through the first threaded part 103A. In still another embodiment shown in FIG. 10, the adjusting screw 72 of the constant-speed exhaust valve device 130 is formed in a double step cylinder, the first threaded part 133A is disposed between a larger diametered top cylinder part 132b and the inner periphery at top end part of the casing 131, and the second threaded part 133B is disposed between a smaller diametered lower cylinder part 132c and the inner periphery at top end part 136a of the push means 136 forming an axial recess accommodating therein the lower cylinder part 132c. In yet another embodiment shown in FIG. 11 according to the present invention, the adjusting screw 162 of the constant-speed exhaust valve device 160 is provided with an outer peripheral wall 162b and a center boss 162c, and, in annular space between the outer peripheral wall 162b and the central boss 162c, both of the top end part 161a of the housing 161 to be coupled to the outer peripheral wall 162b through the first threaded part 163A and the top part 166a of the push means 166 to be coupled to the center boss 162c through the second threaded part 163B are inserted.

In these embodiments of FIGS. 9 to 11, other constituents and functions than those referred to in the above are the same as those in the foregoing embodiments of FIGS. 3 and 4 and FIGS. 7 and 8. In FIGS. 9 to 11, substantially the same constituents as those in FIGS. 3 and 4 and FIGS. 7 and 8 are denoted by the same reference numerals as those used in FIGS. 3 and 4 and FIGS. 7 and 8 but as added by 90 or 30, 120 or 60 and 150 or 90, respectively.

Figure 12:
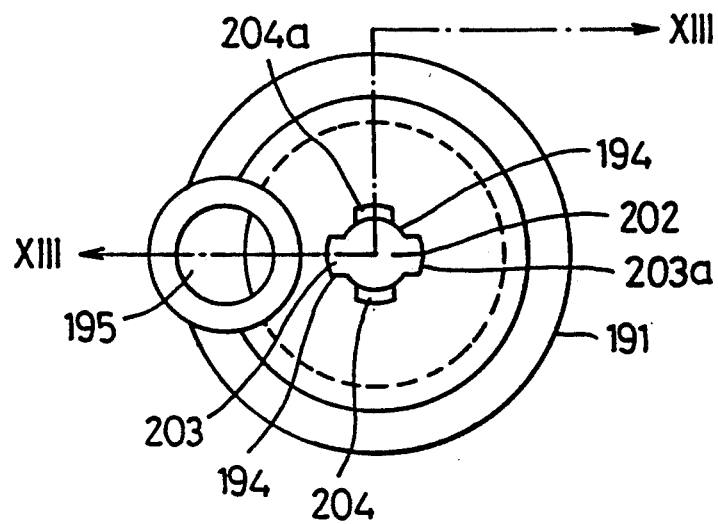
FIG. 12 shows in a bottom plan view a further embodiment of the device according to the present invention.
Figure 13:
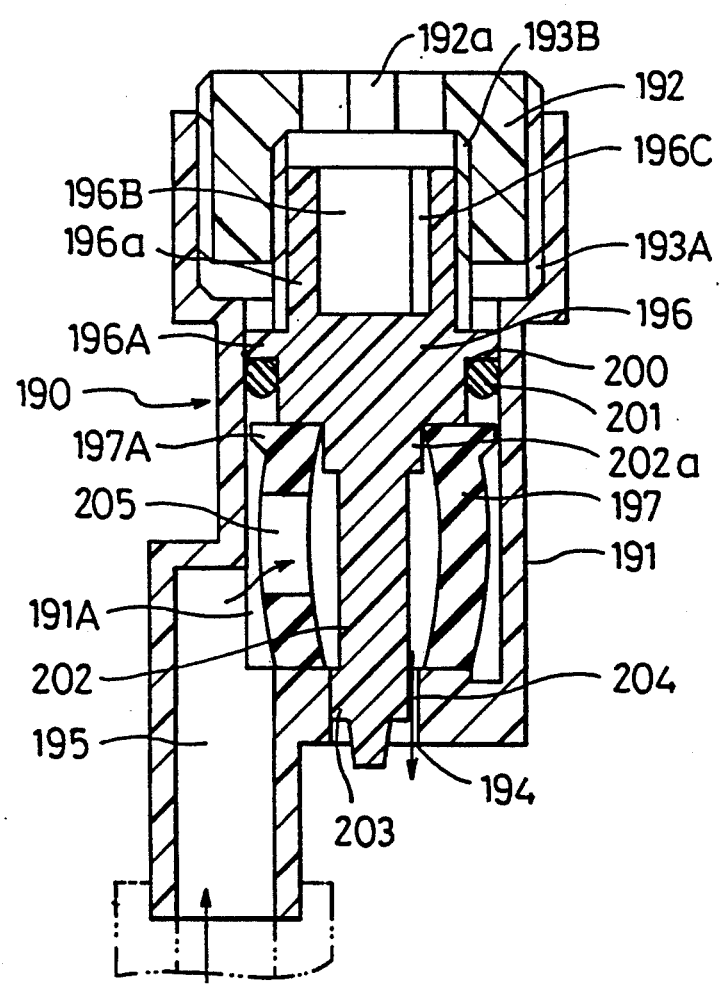
FIG. 13 is sectioned view of the device shown in FIG. 12, taken along line XIII—XIII in FIG. 12.
Figure 14:
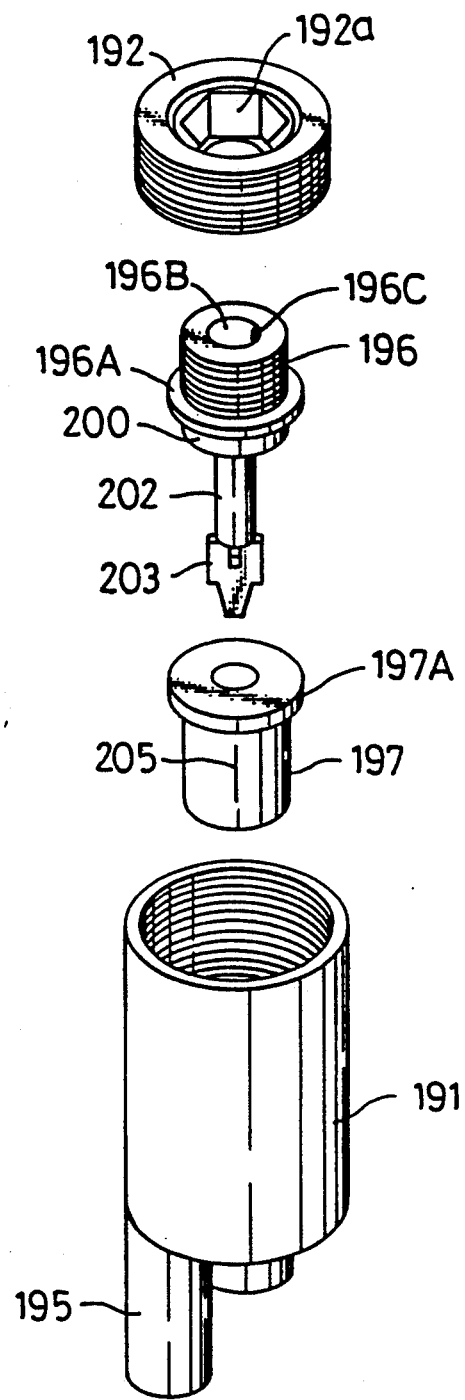
FIG. 14 is a perspective view as disassembled of the device shown in FIG. 12.

Referring next to FIGS. 12 to 14, there is shown a further embodiment of the constant-speed exhaust valve device according to the present invention, in which valve device 190 the valve body 197 is provided at its top end part with an annular outward rib 197A. While the manufacturing of this valve body 197 may be realized with a single metal mold as has been partly described in the foregoing embodiments, a metal mold capable of molding a large number of mold products would be generally employed for manufacturing this type of parts. In this case of the molding, the rib 197A is disposed at a location where the respective valve bodies 197 in the molded article including the large number of the just molded valve bodies 197 are mutually separated into pieces. While in an event where the rib 197A is not provided there has been a risk that the valve body which is relatively thin is caused to be uneven in the thickness due to uneven fins or flashes yielded around cut portions made upon separating the respective valve bodies into pieces from the molded article in which a plurality of the valve bodies are coupled so that the deformation under the compressive force may become irregular so as not to be able to attain the predetermined operation, the provision of the rib 197A to the valve body 197 allows the valve body to have a circumferentially thick portion at the separating cut portion so that, even in the presence of uneven flushes, they will give no influence on the deformation of the valve body 197 and the predetermined operation of the valve body 197 can be expected.

Further, while the present embodiment is similar to that of FIGS. 7 and 8 in which the push means includes the O-ring disposed in the annular recess in the outer periphery for achieving the air tightness of the lower interior space with respect to the upper space in respect of the push means, the present embodiment employs the push means 196 having only an annular flange 196A at an intermediate position so that the rib 197A of the valve body 197 will oppose this annular flange 196A so as to define between them an annular space 200 in which the O-ring 201 can be located. In contrast to the foregoing arrangement in which the annular recess is provided for receiving therein the O-ring, the present instance in which the O-ring 201 may only be required to be disposed below the annular flange 196A of the push means 196 is much more excellent in the assembling ability, than in the case of, typically, the embodiment of FIGS. 7 and 8. Further, in the present instance, the push means 196 is formed to have a jig-inserting axial recess 196B at the top part 196a for allowing an access to the push means 196 through a through hole 192a made in the top of the adjusting screw 192, and it is preferable that an inward projection 196c is provided in the recess 196B, so that the projection 196c will act to prevent the jig inserted in the recess 196B from slipping therein.

In the embodiment of FIGS. 12 to 14, all other constituents and functions than those described above are the same as those in the embodiments of FIGS. 3 and 4 and FIGS. 7 and 8, and the same constituents as those in FIGS. 3 and 4 and FIGS. 7 and 8 are denoted in FIGS. 12 to 14 by the same reference numerals as those used in FIGS. 3 and 4 and FIGS. 7 and 8 but as added by 180 or 120.

What is claimed is:

1. A constant-speed exhaust valve device comprising a valve body made of an elastic material and having a slit of which opening rate is variable in response to a fluid pressure applied to outer side of the body, a push means disposed for pushing said valve body to adjust said opening rate of said slit of the valve body, and a casing in which said valve body and push means are disposed axially movable and having an inlet port to be coupled to a cuff of an associated hemadynamometer and an exhaust port opened to the atmosphere, wherein said valve body is provided in a cylindrical shape opened at both axial ends, and said push means is provided for applying an axial compressive force to said valve body.

2. The device according to claim 1, wherein said push means comprises at least an adjusting screw and a push member made not rotatable about the axis but movable in axial direction.

3. The device according to claim 1, wherein said push means includes an adjusting screw and a spring disposed between the push means and said adjusting screw.

4. The device according to claim 2, wherein said casing is formed in a cylindrical shape opened at one end for accommodating therein said adjusting screw and push member from said open end, and an air-tight sealing means independent of said valve body is disposed between said casing and said push member.

5. The device according to claim 2, wherein said push means includes first and second threaded parts which have mutually the same threaded direction but different tooth pitch, said first threaded part coupling between said casing and said adjusting screw and said second threaded part coupling between said adjusting screw and said push member.

6. The device according to claim 2, wherein said push means includes first and second threaded parts which have mutually opposite threaded direction, said first threaded part coupling between said casing and said adjusting screw, and said second threaded part coupling between said adjusting screw and said push member.

7. The device according to claim 2, wherein said valve body is air-tightly engaged at one end to said push member and at the other end to inner wall surface of said casing.

8. The device according to claim 1, wherein said valve body is provided at one end part circumferentially with an annular rib.

9. The device according to claim 4, wherein said air-tight sealing means comprises an O-ring mounted on outer periphery of said push member, said outer periphery having a flange part for engaging with said O-ring.

* * * * *